United States Patent [19]

Dixon et al.

[11] Patent Number: 4,914,126
[45] Date of Patent: Apr. 3, 1990

[54] AROMATIC AMINES

[75] Inventors: John Dixon, Great Dalby Nr. Melton Nowbray; Francis Ince, Loughborough, both of England

[73] Assignee: Fisons plc, Leicestershire, United Kingdom

[21] Appl. No.: 102,781

[22] Filed: Sep. 23, 1987

Related U.S. Application Data

[63] Continuation of Ser. No. 653,239, filed as PCT GB84/00011 on Jan. 20, 1984, published as WO84/02904 on Aug. 2, 1984, abandoned.

[30] Foreign Application Priority Data

Jan. 21, 1983 [GB] United Kingdom ............... 8301749
Jan. 21, 1983 [GB] United Kingdom ............... 8301751

[51] Int. Cl.$^4$ ................. A61K 31/38; A61K 31/135; A61K 31/40
[52] U.S. Cl. ..................... 514/438; 514/445; 514/471; 514/427; 514/425; 514/424; 514/654; 514/651; 564/357; 564/370
[58] Field of Search ............... 514/438, 445, 471, 427, 514/425, 424, 654, 651

[56] References Cited

U.S. PATENT DOCUMENTS

| | | | |
|---|---|---|---|
| 2,739,981 | 3/1956 | Szabo et al. | 564/370 X |
| 3,013,020 | 12/1961 | Fancher | 564/367 X |
| 3,772,370 | 11/1973 | Surrey | 564/367 |
| 3,808,212 | 4/1974 | Renth et al. | 564/370 X |
| 3,960,959 | 6/1976 | Pless | 564/367 |
| 4,024,281 | 5/1977 | Colella et al. | 564/367 X |

Primary Examiner—Frederick E. Waddell
Attorney, Agent, or Firm—Marshall, O'Toole, Gerstein, Murray & Bicknell

[57] ABSTRACT

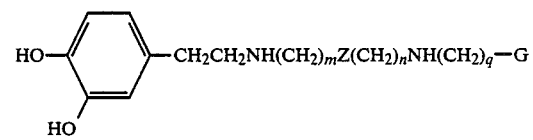

I

Compounds of formula (I), in which Z represent O, S, SO$_2$, CO, NR or a single bond, G represents a one or two ring, saturated or unsaturated carbocyclic or heterocyclic group optionally substituted by phenyl thrihalomethyl or at least groups selected from alkoxy C1 to 6 or halogen atoms, provided that when Z represents a single bond G does not represent phenyl, R represents hydrogen or alkyl C1-6, m and n each independently represent 2, 3 or 4, and q represents an integer from 1 to 3 inclusive, and pharmaceutically acceptable derivatives thereof. There are also described processes for producing the compounds and pharmaceutical, e.g. cardiac, compositions containing them.

7 Claims, No Drawings

AROMATIC AMINES

This application is a continuation of application Ser. No. 653,239, filed as PCT GB 84/00011 on Jan. 20, 1984, published as WO84/02904 on Aug. 2, 1984, now abandoned.

This invention relates to new compounds, processes for their preparation and compositions containing them.

According to the invention we provide the compounds of formula I,

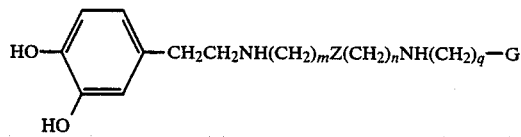

in which Z represents O, S, $SO_2$, CO, NR or a single bond, G represents a one or two ring, saturated or unsaturated carbocyclic or heterocyclic group, G being optionally substituted by phenyl, trihalomethyl or at least two groups selected from alkoxy C1 to 6 or halogen atoms, provided that when Z represents a single bond G does not represent phenyl, R represents hydrogen or alkyl C1-6, m and n each independently represent 2, 3 or 4, and q represents an integer from 1 to 3 inclusive, and pharmaceutically acceptable derivatives thereof.

According to our invention we also provide a process for the production of a compound of formula I, or a pharmaceutically acceptable derivative thereof, which comprises (a) selectively reducing a compound of the formula II,

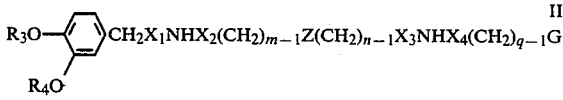

in which $R_3$ and $R_4$, which may be the same or different, each represent hydrogen or a protecting group, one of the pairs $X_1$ and $X_4$, $X_2$ and $X_3$, $X_1$ and $X_3$, and $X_2$ and $X_4$, each represent CO, and the remainder of $X_1$, $X_2$, $X_3$ and $X_4$ each represent $CH_2$, and m, n, q, G and Z are as defined above, and if necessary or desired thereafter, removing any protecting groups to give the corresponding compound of formula I, (b) producing a compound of formula I, in which Z represents $SO_2$, by selectively oxidizing a compound of formula I, or a protected derivative thereof, in which Z represents S, and if necessary or desired thereafter, removing any protecting groups to give the corresponding compound of formula I, or (c) removal of a protecting group from a corresponding compound of formula I carrying one or more protected hydroxy or protected amine groups, and where desired or necessary converting the resulting compound of formula I to a pharmaceutically acceptable derivative thereof, or vice versa.

In process (a), the reducing agent may be electrophilic, for example diborane, or nucleophilic, for example a complex metal hydride, e.g. lithium aluminium hydride or sodium (2-methoxyethoxy)aluminium hydride. The reaction may be carried out in a suitable solvent inert to the reaction conditions. Aprotic solvents are preferred, for example tetrahydrofuran, diethyl ether, or 1,2-dimethoxyethane. The reaction may be carried out at a temperature of from 0° to 100° C.

When $R_3$ and/or $R_4$ represent a protecting group, the protecting group may be for example alkyl C1-6, phenylalkyl C7-12, e.g. benzyl, or alkanoyl C2-6, e.g. acetyl.

Removal of the protecting group depends on the nature of the protecting group; conventional techniques may generally be employed, including acidic or basic cleavage, or hydrogenolysis. For example, protecting alkyl or phenylalkyl groups may be removed by cleavage using a protic acid, e.g. hydrochloric acid or hydrobromic acid at a temperature of 0° to 150° C., or a Lewis acid, e.g. by reacting with a boron trihalide in a halocarbon solvent. When the protecting group is alkanoyl, cleavage may be effected using a base, e.g. sodium hydroxide, in a suitable solvent, e.g. aqueous ethanol. Lewis bases, e.g. pyridine hydrochloride, may be used to cleave alkyl or phenylaklyl groups. 1-Phenylalkyl groups, e.g. benzyl, may be removed by catalytic hydrogenation using a suitable catalyst, e.g. palladium, in a suitable solvent, e.g. ethanol, or acetic acid.

Oxidising agents that may be used in process (b) include hydrogen peroxide and organic peracids, e.g. m-chloroperbenzoic acid. The reaction may be carried out in a suitable solvent inert to the reaction conditions, e.g. a halogenated hydrocarbon solvent. Particular solvents that may be mentioned include dichloromethane and 1,2-dichloroethane. The reaction may be carried out at a temperature of from 0° to 100° C. The reaction may be carried out on a suitable unprotected derivative of the compound of formula I. However we prefer the starting compound to have the nitrogen and/or oxygen groups bearing protecting groups. Suitable protecting groups for oxygen include those listed above for $R_3$ and $R_4$; groups that may be particularly mentioned are alkyl C1 to 6, e.g. methyl, and phenylalkyl C7 to C12, especially benzyl. Suitable protecting groups for nitrogen include alkanoyl groups, e.g. alkanoyl C2-6. A particular group that may be mentioned is trifluoroacetyl. The protecting groups may be removed by conventional techniques well known in the art.

The removal of protecting groups, in process (c) may be carried out as described for process (a), under acidic, basic or hydrogenolytic conditions. The compound of formula I may have protected hydroxy and/or amino groups. Such groups, their application, and their removal, are well known and include those described in Protective Groups in Organic Chemistry, Ed: J. F. W. McOmie, Plenum Press (1973) and Protective Groups in Organic Synthesis, T. W. Greene, Wiley-Interscience (1981).

The preparation of compounds of formula II depends on the nature of $X_1$, $X_2$, $X_3$ and $X_4$.

When $X_1$ and $X_4$ both represent CO, and $X_2$ and $X_3$ both represent $CH_2$, the compounds of formula II may be made by sequentially reacting a compound of formula III,

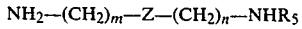

where $R_5$ represents hydrogen or a nitrogen protecting group removable in the presence of an amide bond, alkylene CONH alkylene, and m, n and Z are as defined above, with the compounds of formulae IV and V,

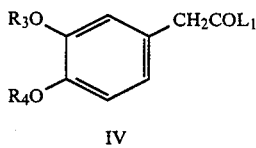   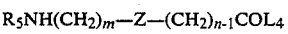

IV                                V in any order,
wherein $L_1$ and $L_2$ represent good leaving groups, and q, G, $R_3$ and $R_4$ are as defined above.

Suitable nitrogen protecting groups $R_5$ are well known in the art of peptide synthesis, and include for example alkoxycarbonyl groups, e.g. ethoxycarbonyl.

Good leaving groups $L_1$ and $L_2$ include, for example, halogen, e.g. chlorine or bromine; 1-imidazolyl, trifluoromethane sulphonate, alkyl carbonate, e.g. ethyl carbonate; venzyl carbonate; alkanoyloxy, e.g. acetyl; or trifluoracetoxy.

The reaction may be carried out in a solvent which is inert to the reaction conditions, for example a chlorinated hydrocarbon, e.g. chloroform, in the presence of a non-nucleophilic base, e.g. triethylamine. The reaction may be carried out at a temperature of from about 0° to 100° C.

The free acids corresponding to the compounds of formula IV and V, i.e. when $L_1$ and $L_2$ both equal hydroxy may be reacted, e.g. with thionyl chloride, ethyl chloroformate, or N,N'-carbonyldiimidazole to convert the carboxyl groups to a group —$COL_1$ or —$COL_2$ respectively. When $X_2$ and $X_3$ both represent CO, and $X_1$ and $X_4$ both represent $CH_2$, the compounds of formula II may be prepared by sequentially reacting the groups $L_3$ and $L_4$, in any order, in the compound of formula VI, $$L_3CO-(CH_2)_{m-1}-Z-(CH_2)_{n-1}-COL_4 \quad VI$$

in which $L_3$ represents a good leaving group, and $L_4$ represents either a good leaving group, or a group which may be readily converted into a good leaving group, and m, n and Z are as defined above, with the compounds of formula VII and VIII,

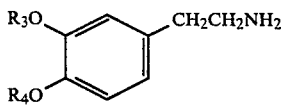

VII                               VIII wherein q, G, $R_3$ and $R_4$ are as defined above.

Good leaving groups that $L_3$ and $L_4$ may represent include those described above for $L_1$ and $L_2$. When $L_4$ represents a group which may be converted into a good leaving group, such convertible groups include alkoxy, ethoxy, methoxy; and hydroxy. The conversion may be effected using conventional techniques.

We prefer to carry out the sequential replacement of $L_3$ and $L_4$ as follows: with $L_4$ as a group convertable to a leaving group, $L_3$ may be reacted with a compound of formula VII or formula VIII. $L_4$ is then converted to a good leaving group, and reacted with the remaining compound of formula VII or formula VIII.

The reactions may be carried out under conditions similar to those described above when $X_1$ and $X_4$ both represent CO.

When both $X_1$ and $X_3$, or both $X_2$ and $X_4$ represent CO, and the remainder of $X_1, X_2, X_3$ and $X_4$ represent $CH_2$, the corresponding compounds of formula II may be made by sequential reaction in any order with the nitrogen function and the carbonyl function of the compound of formula IX, $$R_5NH(CH_2)_{m-1}-Z-(CH_2)_{n-1}COL_4 \quad IX$$

wherein $R_5$, $L_4$, m, n and Z are as defined above, with the compounds of either formula IV and formula VIII, or the compounds of formula VII and formula V, as defined above.

A typical procedure is as follows: with $L_4$ as a leaving group and $R_5$ as a protecting group, a compound of formula IX may be reacted with a compound of formula VIII, followed by conversion of $R_5$ from a protecting group to a hydrogen, and the process is concluded by reacting this compound with a compound of formula IV, to give a compound of formula II in which $X_1$ and $X_3$ each represent CO, and $X_2$ and $X_4$ represent $CH_2$.

The reactions may be carried out under conditions similar to those described above for the preparation of compounds of formula II when $X_1$ and $X_4$ both represent CO.

The compounds of formulae III, IV, V, VI, VII, VIII and IX are either known, or may be made from known compounds using techniques known per se.

The acid addition salts of the compounds of formula I may be prepared by reaction of the free-base with an appropriate acid. The acid addition salts may be converted to the corresponding free-base by the action of a stronger base.

The processes as described above may produce the compound of formula I or a derivative thereof. It is also within the scope of this invention to treat any derivative so produced to liberate the free compound of formula I, or to convert one derivative into another.

The compounds of formula I and the intermediates therefore may be isolated from their reaction mixtures using conventional techniques.

Pharmaceutically acceptable derivatives of the compounds of formula I include pharmaceutically acceptable acid addition salts. Suitable salts include salts of mineral acids, for example, hydrophalic acids, e.g. hydrochloric acid or hydrobromic acid; or organic acids, e.g. formic, acetic or lactic acids. The acid may be polybasic, for example sulfuric, fumaric or citric acid.

Other pharmaceutically acceptable derivatives are compounds which will be suitable bioprecursors (prodrugs) of the compounds of formula I nd will be readily apparent to those skilled in the art and may be made from the compounds of formula I using conventional processes known per se or by processes analogous to those described above. Suitable bioprecursors include amides e.g. acetamides or benzamides of compounds of formula I, and esters, for example, carboxylic acid esters, e.g. alkanoyl, such as acetyl or isobutyryl, or aroyl, e.g. benzoyl.

One or two ring, saturated or unsaturated, carbocyclic or heterocyclic groups that G may represent include phenyl, cyclohexyl, cyclohexenyl, naphthyl, 1,2,3,4-tetrahydronaphthyl, decalyl, pyridyl, quinolyl, piperidinyl, pyrrolo, pyrrolidinyl, thiophenyl and furanyl.

A preferred group of compounds of formula I are those
in which Z represents O, S, $SO_2$, CO or NR,
R represents hydrogen or alkyl C1 to 6, m and n each represent 2, 3 or 4, and q represents an integer from 1 to 3 inclusive, and pharmaceutically acceptable derivatives thereof.

We particularly prefer Z to represent O, S or $SO_2$.

A further preferred group of compounds of formula I are those in which Z represents a single bond, G represents naphthyl, thiophenyl, cyclohexenyl, cyclohexyl or phenyl, the phenyl being substituted by phenyl or trihalomethyl or by at least two alkoxy C1 to 6 or by at least two halogen atoms, m and n together represent an integer from 4 to 8 inclusive, q represents an integer from 1 to 3 inclusive, and pharmaceutically acceptable derivatives thereof.

We particularly prefer G to represent naphthyl, thiophenyl, or phenyl, the phenyl being substituted by phenyl or trihalomethyl or by at least two alkoxy C1 to 6 or by at least two halogen atoms.

Specific groups that G may represent include 2-, 3- and especially 4-biphenyl;

2-, 4- and particularly 3-trihalomethyl, e.g.

3-trichoromethyl; 3-trifluoromethylphenyl is especially preferred;

3- and especially 2-thiophenyl;

2- and especially 1-naphthyl; cyclohexyl;

and cyclohexenyl.

When G represents phenyl substituted by at least two alkoxy C1 to 6 groups, the alkoxy groups may be the same or different. In particular, G may represent phenyl substituted by two alkoxy C1 to 6 groups in which the alkoxy groups may be in a 1,2, 1,3 or 1,4 relationship to one another. Preferably G represents 3,4-dialkoxyphenyl, particularly 3,4-dimethoxyphenyl.

When G represents phenyl substituted by at least two halogen atoms, the halogen atoms may be the same, e.g. all chlorine atoms, or different, e.g. selected from fluorine, chlorine, bromine or iodine. In particular, G may represent phenyl substituted by two halogen atoms, in which the halogen atoms may be in a 1,2, 1,3 or 1,4 relationship to one another. Preferably G represents 3,4-dihalophenyl, particularly 3,4-dichlorophenyl.

We prefer compounds of formula I in which m +n is an integer from 4 to 7; and preferably 5 or 6.

We prefer compounds of formula I in which q is 2.

Specific values of m that may be mentioned include 2 and 3. Specific values of n that may be mentioned include 2 and 3.

When R represents alkyl, groups that may be mentioned include methyl, ethyl and propyl.

The compounds of formula I, and pharmaceutically acceptable derivatives thereof, are useful because they possess pharmacological activity in animals. Thus the compounds act on peripheral and/or central dopamine receptors. As such, they lower blood pressure, reduce heart rate and increase blood flow to certain vascular beds, e.g. renal beds. Some compounds also have an action on other adrenoreceptors, and these exhibit cardiac stimulant and bronchodilator effects. Activity of the compounds has been observed in the following assay systems:

(a) canine renal blood flow and canine femoral blood flow, McNay and Goldberg, J. Pharmac, Exp. Ther., 151, 23-31, 1966.

(b) rabbit isolated ear artery, McCullogh, Rand and Story, Br. J. Pharmac, 49, 141-142, 1973, and (c) cat nictitating membrane, Gyorgy and Doda, Arch. Int. Pharmacodyn, 226, 194-206, 1977.

The compounds of the invention are indicated for use in the treatment of congestive heart failure, renal failure, angina pectoris, ischaemic heart disease, hypertension and reversible obstructive airways disease, hyperprolactinaemia and also in Parkinson's disease and other neurological disorders.

The dosage administered will naturally depend on the compound employed, the mode of administration and the desired effect. However, in general, satisfactory results are obtained when the compounds are administered at a dosage of from 0.05 $\mu$g to 50 mg per kilogram of body weight per day. For man, the indicated total daily dosage is in the range 2.5 $\mu$g to 3.5 g, which may be administered in divided doses of, for example 1 $\mu$g to 750 mg.

The new compounds of the present invention may be used in combination with, or sequentially with, a wide variety of other pharmaceutically active substances. Where appropriate the compounds may be mixed with one or more other active substances. The particular mixture or dose regimen used, and ratio of the active ingredients will depend on a variety of factors including the condition to be treated, the mode of administration, the particular active ingredients and the patient concerned.

Examples of compounds with which the present compounds may be mixed include:

beta-blockers, especially cardioselective beta blockers, for example, atenolol;

diuretics, for example thiazides, e.g. furosemide;

angiotensin converting enzyme inhibitors, for example captopril;

inotropic agents, for example, amrinone;

antiemetics, for example, sulpiride, metoclopramide, or domperidone.

The compounds of formula I, and pharmaceutically acceptable derivatives thereof, have the advantage that they are more efficacious or produce less undesirable side effects in certain pharmacological models, or are longer acting than compounds of similar structure to the compounds of formula I.

The compounds of the invention may be administered by a wide variety of routes and may act systemically or locally. Thus the compounds may be administered by oral or nasal inhalation to the lung, to the buccal cavity, oesophageally, rectally, topically to the skin or to other available surfaces of the body, by injection, e.g. intravenously, intramuscularly, intraperitoneally, or by surgical implant.

According to our invention we also provide a pharmaceutical composition comprising preferably less than 80% and more preferably less than 50% by weight of a compound of formula I, or a pharmaceutically acceptable derivative thereof, in admixture with a pharmaceutically acceptable adjuvant, diluent or carrier. Examples of suitable adjuvants, diluents or carriers are: for tablets, capsules and dragees; microcrystalline cellulose, calcium phosphate, diatomaceous earth, a sugar such as lactose, dextrose or mannitol, talc, stearic acid, starch, sodium bicarbonate and/or gelatin;

for suppositories; natural or hardened oil or waxes, and for inhalation compositions, coarse lactose.

When the compounds are to be used in aqueous solution it may be necessary to incorporate a chelating or sequestering agent, e.g. sodium edetate, an antioxidant, e.g. sodium metabisulphite or buffering agents, e.g. sodium hydrogen phosphate and sodium phosphate.

Aqueous solutions typically contain up to about 10% w/w of the new compound and may be used for intravenous injections.

According to the invention, we further provide a method of increasing the force of contraction of the heart in an animal, either human or non-human, which method comprises administering to the animal an effective amount of one or more compounds of the invention.

The invention is illustrated, but in no way limited by the following examples, in which temperatures are in degrees centigrade.

EXAMPLE 1

4-(2-(2-(3-(2-Phenylethylamino)propylthio)ethylamino) ethyl-1,2-benzenediol

(a) 3(Methoxycarbonylmethylthio)propionic acid

A mixture of β-propiolactone (15.2 ml, 0.24 mole) and methylthioglycollate (43.3 ml, 0.55 mole) was heated on a steam bath for 72 hr under nitrogen. The cooled reaction mixture was dissolved in ether and extracted with saturated aqueous sodium bicarbonate solution (2×50 ml). The combined aqueous extracts were washed with ether (2×100 ml) acidified with 2N hydrochloric acid (pH and extracted with ethyl acetate (5×100 ml). The combined organic extracts were washed with water and brine, dried ($Na_2SO_4$) and evaporated to give the sub-title compound as a colourless oil (40.1 g, 94%) nmr ($CDCl_3$) δ: 2.6–3.2, 4H,m,; 3.3, 2H,s; 3.8, 3H,s; 11.55, 1H, s exchanged with $D_2O$.

(b) 3-(2-Oxo-2-(2-(3,4-dimethoxyphenyl)ethylamino)ethylthio)-N-(2-phenylethyl)propamamide.

The product from step a (10.0 g, 0.0562 mole) was dissolved in dry dichloromethane 300 ml) and N,N-carbonyldiimidazole (9.4 g, 0.058 mole) added in portions under nitrogen with stirring. Stirring was continued for 4 hr and 2-phenylethylamine (7.0 ml, 0.0562 mole) was added and the mixture stirred for 18 hr. The solution was washed with 2N hydrochloric acid, water, saturated aqueous sodium bicarbonate solution, and water, dried ($Na_2SO_4$) and evaporated to give a yellow oil (13.3 g) mass spectrum M+ $m/e$ 281.

A portion of this oil (12.8 g) was dissolved in methanol (100 ml) and to this solution was added water (50 ml) and saturated aqueous sodium bicarbonate (100 ml) and the mixture heated to reflux for 3 hr. The majority of the methanol was removed in vacuo and the aqueous residue washed with ether (discarded), acidified and extracted with ethyl acetate (4×100 ml). The combined extracts were washed with water, dried ($Na_2SO_4$) and evaporated. The residue was triturated with ether to give a solid (7.9 g), mass spectrum M+ $m/e$ 267.

This solid was dissolved in dry dichloromethane (300 ml), N,N-carbonyldiimidazole (5.13 g) was added and the solution stirred for 3 hr under nitrogen. 2-(3,4-Dimethoxyphenyl)ethylamine (5.13 g) was added and the solution stirred for 18 hr, washed with 2M hydrochloric acid, water, saturated sodium bicarbonate solution and water, dried ($Na_2SO_4$) and evaporated. The residue was recrystallised from methanol to give the sub title compound as a cream solid (10.9 g, 38%); mp 156°–8°.

(c) 3-(2-(2-(3,4-D!methoxyphenyl)ethylamino)ethylthio)-N-(2-phenylethyl)propanamide dihydrochloride A mixture of the product from step b (5.2 g–0.012 mole) and diborane (70 ml of 1M solution in tetrahydrofuran) in tetrahydrofuran (200 ml) was heated to reflux for 5 hr with stirring under nitrogen. Methanol was added to the cooled reaction mixture and the solution stirred for 18 hr. The solvents were evaporated and the residue treated with a saturated solution of hydrogen chloride gas in methanol. The mixture was heated to reflux for 1 hr, the solvents evaporated and the residue recrystallised from methanol to give the sub title compound as a white solid (4.75 g, 83%); mp 241°–4°.

(d) 4-(2-(2-(3-(2-Phenylethylamino)propylthio)ethylamino) ethyl-1,2-benzenediol dihydrobromide The product from step (c) (3.5 g–0.0074 mole) was suspended in dry dichloromethane (200 ml) and the mixture cooled to −70° Boron tribromide (4.0 ml, 0.042 mole) was added and the mixture stirred for 5 hr under nitrogen whilst warming to room temperature. Methanol was added and the mixture stirred for 18 hr. The solvents were evaporated and the residue recrystallised twice from ethanol to give the dihydrobromide of the title compound as a white solid (3.2 g, 81%); mp 157–9°.

EXAMPLE 2

4-(2-(2-(3-(2-Phenylethylamino)ethylthio)propylamino) ethyl-1,2-benzenediol

(a) N-(2-(3,4-Dimethoxyphenyl)ethyl-3-(2-oxo-2-(2-phenylethylamino)ethylthiopropanamide The subtitle compound was prepared by the method of Example 1(b), mp 153°–5°.

(b) N-(2-(3,4-Dimethoxyphenyl)ethyl-3-(2-(2-phenylethylamino)ethylthiopropanamine dihydrochloride The subtitle compound was prepared by the method of Example 1(c), mp 242°–5°.

(c) 4-(2-(3-(2-(2-phenylethylamino)ethylthio)propylamino) ethyl-1,2-benzenediol dihydrobromide The title compound was prepared as a dihydrobromide, by the method of Example 1(d), mp 156°–9°.

EXAMPLE 3

4-(2-(2-(3-(2-Phenylethylamino)propoxy)ethylamino) ethyl)-1,2-benzenediol

(a) 3-(2-Oxo-2-(2-(3,4-dimethoxyphenyl)ethylamino)ethoxy)-N-(2-phenylethyl)propanamide The sub title compound was prepared by the method of Example 1(b), mp 108°–10°.

(b) 3-(2-(2-(3,4-Dimethoxyphenyl)ethylamino)ethoxy)-N-(2phenylethyl)propanamine dihydrochloride The subtitle compound was prepared by the method of Example 1(c), mp 207°–10°.

(c)

4-(2-(2-(3-(2-Phenylethylamino)propoxy)ethylamino)ethyl)-1,2-benzenediol

The title compound was prepared as a dioxalate, by the method of Example 1(d), mp 149°–51°.

EXAMPLE 4

4-(2-(3-(2-(2-Phenylethylamino)ethoxy)propylamino)ethyl)-1,2-benzenediol (a)

3-(2-oxo-2-(2-phenylethylamino)ethoxy)-N-(2-(3,4dimethoxyphenyl ethylpropanamide mp 107°–110°

(b) N-(2-(3,4-dimethoxyphenyl)ethyl)-3-(2-(2-phenyl ethylamino)ethyl) propanamine dihydrochloride The subtitle compound was prepared by the method of Example 1(c), mp 194°–7°.

(c)

4-(2-(3-(2-(2-phenylethylamino)ethoxy)propylamino)ethyl)-1,2-benzenediol

The title compound was prepared by the method of Example 1(d), as a dihydrobromide, mp.

EXAMPLE 5

4-(2-(2-(3-(2-Phenylethylamino)propanesulphonyl)-ethylamino)ethyl)-1,2-benzenediol (a) 3,4-Dimethoxy-N-(2-(3-(2-phenylethylamino)propylsulphonyl)ethyl)-benzeneethanamine dihydrochloride A solution of trifluoroacetic anhydride (2.0 ml, 2.97 g, 14.1 moles) in dry dichloromethane (20 ml) was added dropwise with stirring to the product from Ex 1(c) (1.8 g, 3.8 mmoles) and triethylamine (1.6 ml, 11.5 mmoles) in dry dichloromethane (100 ml). The mixture was stirred for 3 hours, then washed with dilute hydrochloric acid, dilute sodium bicarbonate solution and water and dried (Na$_2$SO$_4$). This solution of the bis trifluoroacetyl derivative was cooled to 0° and treated with stirring with m-chloroperoxybenzoic acid (1.38 g, 8.0 mmoles). The solution was allowed to warm to room temperature and stirred for 1.5 hours, then washed with 2% w/v sodium bisulphite solution and saturated sodium bicarbonate solution, dried and evaporated to give the N,N'-bis trifluoroacetyl derivative of the sub-title product as a glassy semi-solid (2.3 g). This crude material was dissolved in methanol (30 ml) and potassium carbonate (1.04 g, 7.5 mmoles) in water added. The dark mixture was boiled under reflux for 2.5 hr, then the bulk of the methanol was removed by distillation under vacuum. The aqueous residue was extracted with ethyl acetate and the extracts were dried and evaporated to an oil, which was dissolved in ethanol (20 ml) and treated with concentrated hydrochloric acid (1 ml). The white precipitate was collected and recrystallised from ethanol-water giving sub-title compound (1.31 g) as colourless crystals mp 246°–8° (decomp).

(b)

4-(2-(2-(3-(2-Phenylethylamino)propanesulphonyl)-ethylamino)ethyl)-1,2-benzenediol dihydrobromide The product of step (a) above (1.5 g) in 48% aqueous hydrobromic acid (15 ml) containing aqueous hypophosphorous acid (5 drops) was heated at reflux under nitrogen for 4 hr. The soluton was cooled and crystals which separated were filtered and washed with cold ethanol and ether to give the dihydrobromide as the title compound (1.2 g) m.p. 190°–191° (from 2-propanol-methanol).

EXAMPLE 6

The following compound was made by methods analogous to those described in Example 5:

4-(2-(3-(2-(2-Phenylethylamino)ethanesulphonyl) ethylamino)ethyl)-1,2-benzenediol dihydrobromide m.p. 191.5°–193.5°.

EXAMPLE 7

4-(2-(6-(2-(3,4-Dimethoxyphenyl)ethylamino)hexylamino) ethyl)-1,2-benzenediol (a)

N(2-(3,4-bisphenylmethoxy)ethyl)-N'-2-(3,4dimethoxyphenyl)ethyl)hexan-1,6-diamide.

To a solution of 6-(2-(3,4-dimethoxyphenyl)ethylamino-6-oxohexanoic acid (3.93 g, 0.0127 mole) in dry dichloromethane (100 ml) was added triethylamine (3.22 mg, 4.4 ml, 0.032 mole) and ethylchloroformate (1.38 g, 1.21 ml, 0.0127 mole) with stirring and cooling. The solution was stirred at room temperature for 1 hour and 2-(3,4-bis (phenylmethoxy)phenyl)ethylamine hydrochloride (4.71 g–0.0127 mole) added and the solution stirred at room temperature for 20 hours. The reaction mixture was washed with 2N hydrochloric acid (3×100 ml), 5% w/v sodium hydroxide solution (2×100 ml) and water (2×100 ml), dried (Na$_2$SO$_4$) and evaporated. The residue was recrystallised from 2-propanol to give a white solid (6.23 g, 77%); mp 151°–2°.

(b)

N-(2-(3,4-Bis(phenylmethoxy)ethyl-N$^1$-2-(3,4-dimethylphenyl)ethyl)hexane-1,6-diamine dihydrochloride The product from step (a) (5.5 g, 0.0086 mole) was dissolved in dichloromethane (100 ml) and to this solution was added a solution of lithium aluminium hydride (34 ml of 1M solution, 0.034 mole) and the mixture heated to reflux for 18 hours. 10% w/v sodium hydroxide solution was added cautiously, the organic layer separated and the aqueous layer extracted with dichloromethane (2×20 ml). The combined organic extracts were washed with water, dried (Na$_2$SO$_4$) and evaporated. The residue was dissolved in warm methanol saturated with hydrogen chloride gas and then the solvents were evaporated. The residue was recrystallised from methanol to give a white solid (2.51 g 42%); mp 238°–40°.

(c)

4-(2-(6-(2-(3,4-dimethoxypbenyl)ethylamino)hexylamino) ethyl)-1,2-benzenediol dihydrochloride The product from step (b) (2.41 g, 0.0036 mole) was dissolved in methanol (200 ml) and hydrogenated at room temperature and pressure in the presence of 10% palladium on carbon (0.4 g). The catalyst was removed by filtration, the filtrate evaporated and the residue triturated with hot 2-propanol to induce crystallisation. The solvent was removed in vacuo and the residue recrystallised from ethanol to give the dihydrochloride of the title compound as a white solid (1.30 g, 73%); mp 188°–91°

EXAMPLE 8

4-(2-(6-(2-(2-Thienyl)ethylamino)hexylamino)ethyl)-1,2-benzenediol (a)

N-(2-(3,4-Dimethoxyphenyl)ethyl)-N'-(2-(2-thienyl)ethyl hexane-1,6-diamide

This was prepared from 6-(2-(3,4-dimethoxyphenyl)ethyl amino-6-oxohexanoic acid and 2-thiopheneethanamine by the method of Example 7 (a) above.

(b)

N-(2-(3,4-Dimethoxyphenyl)ethyl-N'-2-(2-thienyl)ethyl hexane-1,6-diamine

Boron trifluoride etherate (8.5 g) in dry tetrahydrofuran (50 ml) was added dropwise with stirring to the product from step (a) (4.3 g) and sodium borohydride (1.75 g) in dry tetrahydrofuran (200 ml). The resulting suspension was heated at reflux for 8 hours under nitrogen. Methanol was then added cautiously and the solution evaporated to dryness. The residue was heated at reflux for 30 minutes in methanol (100 ml) saturated with hydrogen chloride gas. The solution was cooled, to give on filtration, the dihydrochloride of the sub title compound, (2.2 g), mp 269.5-271.5 (from methanol).

(c) 4-(2-(6-(2-(2-Thienyl)ethylamino)hexylamino)ethyl)-1,2-benzediol

The product of step (b) (2.2 g) in dry triethylamine (1.06 g) in dry dichloromethane (100 ml) was cooled to −70° and boron tribromide (4.76 g) was added under nitrogen. The resulting suspension was stirred at −70° for 1 hour and then allowed to warm to ambient temperature overnight. Excess methanol was added cautiously, the solution taken to dryness and the residue crystallised by trituration with dry ethanol and dry ether. The resulting deliquescent solid was dissolved in water and neutralised with saturated aqueous sodium bicarbonate solution. The precipitated, air-sensitive base was filtered, washed with water, ethanol and ether and was then dissolved in boiling methanol (50 ml) and treated with a solution of oxalic acid (1 g) in methanol (10 ml). The crystals which separated on cooling (0.5 g) were filtered and washed thoroughly with hot methanol giving the title compound as a dioxalate salt containing 1.5 moles water of crystallisation mp 213°-5°

EXAMPLE 9

4-(2-(6-(2-((1,1'-Biphenyl)-4-yl)ethylamino) hexylamino)ethyl-1,2-benzenediol (a)

N'(2-((1,1'-Biphenyl)-4-yl)ethyl)-N'-(2-(3,4-dimethoxyphenyl)ethyl)hexane-1,6-diamide Triethylamine (5.6 ml, 0.04 mole) was added to a solution of 6-oxo-6-(2-(3,4-dimethoxyphenyl)ethyl) aminohexamoic acid (5.56 g, 0.018 mole) in dry dichloromethane (200 ml). This solution was cooled to 0° and ethylchloroformate (1.8 ml, 0.019 mole) added and the solution stirred for 2 hours at room temperature. 2-((1,1'-Biphenyl)-4-yl)ethylamine hydrochloride (4.4 g, 0.019 mole) was added and the mixture stirred at room temperature overnight. A solid was isolated by filtration washed well with dichloromethane, 2M aqueous hydrochloric acid and water and dried in vacuo. The dichloromethane layer from the filtrate was separated, washed with 2M aqueous hydrochloric acid and water, dried (Na$_2$SO$_4$) and evaporated to give a total yield of 8.8 g. This solid was recrystallised twice from ethanol to give the sub title compound as a white solid (7.3 g, 83%) mp 177°-9°

(b)

N-(2-((1,1'-Biphenyl)-4-yl)ethyl-N'(2-(3,4-dimethoxy phenyl)ethyl)hexane-1,6-diamine The product from step (a) (6.5 g, 0.013 mole) was suspended in dry tetrahydrofuran (200 ml), a solution of diborane in tetrahydrofuran (0.065 mole, 65 ml of 1 molar solution) added and the mixture heated to reflux with stirring under nitrogen for 5 hours after which time the suspended solid had dissolved. Methanol was added cautiously to the cooled reaction mixture and the solution stirred at room temperature for 16 hours. The solvents were removed in vacuo and the residue dissolved in methanol, treated with a solution of hydrogen chloride gas in methanol and the mixture beated to reflux for 2 hours. After cooling the precipitate was isolated by filtration and recrystallised twice from methanol giving the dihydrochloride of the sub title compound as a white solid (5.6 g, 79%, mp 231°-4°).

(c)

4-(2-(6-((1,1'-Biphenyl)-4-yl)ethylamino)hexylamino) ethyl-1,2-benzenediol dihydrobromide The product from step (b) (5.0 g, 0.0094 mole) was heated to reflux with stirring under nitrogen with 48% aqueous hydrobromic acid (100 ml) and hypophosphorous acid (0.1 ml) for 4 hours. The solid precipitated on cooling was isolated, washed with water, dried in vacuo at 80° and recrystallised twice from methanol affording the dihydrobromide of the title product as a white solid (2.6 g, 47%), mp 248°-51°.

EXAMPLE 10

4-(2-(6-(2-(3,4-Dichlorophenyl)ethylamino)hexylamino) ethyl)-1,2-benzenediol (a)

N-(2-(3,4-Dichlorophenyl)ethyl)-N'-(2-(3,4-dimethoxyphenyl)ethyl)hexane-1,6-diamide This was made by the method of Example 7 (a) mp.

(b)

N-(2-(3,4-dichlorophenyl)ethyl)-N'-(2-(3,4-dimethoxyphenyl)ethyl)hexane-1,6-diamine dihydrochloride The product of step (a) was treated by the method of Example 8 (b) to give the sub title compound, mp 275°-277°.

(c)

4-(2-(6-(2-(3,4-dichlorophenyl)ethylamino])exylamino) ethyl)-1,2-benzenediol dihydrobromide The product of step (b) was treated by the method of Example 9 (c) to give the dihydrobromide salt of the title compound, mp 169.5°-171°.

EXAMPLE 11

4-(2-(6-(2-(3-(trifluoromethyl)phenyl)ethylamino) hexylamino)ethyl)-1,2-benzenediol (a)

N-(2-(3,4-Dimethoxyphenyl)ethyl)-N-(2-(3-(trifluoromethyl)phenyl)ethyl)hexane-1,6-diamide This was made by the method of Example 7 (a), mp 125°-6.5°.

(b)
N-(2-(3,4-Dimethoxyphenyl)ethyl)-N-(2-(3-(trifluoromethyl)phenyl)ethyl)hexane-1,6-diamine dihydrochloride This was made by the method of Example 8 (b), mp 239°–241°.

(c) 4-(2-(6-(2-(3-(Trifluoromethyl)phenyl)ethylamino)hexylamino)ethyl)-1,2-benzenediol This was made by the method of Example 9 (c) to give the dihydrobromide of the title compound, mp 235°–237°.

EXAMPLE 12

4-(2-(6-(2-(1-Naphthalenyl)ethylamino)hexylamino)ethyl)-1,2-benzenediol

(a)
N-(2-(3,4-Dimethoxyphenyl)ethyl)-N'-(2-(1-naphthalenyl)ethyl)-hexane 1,6-diamide This sub title compound, mp 155.5°–156.7° was prepared from 6-(2-(3,4-dimethoxyphenyl)ethylamino-6-oxo-hexanoic acid and 2-(1-naphthyl)ethylamine hydrochloride by the method of Example 7 (a).

(b)
N-(2-(3,4-Dimethoxyphenyl)ethyl)-N'-(2-(1-naphthalenyl)ethyl)-hexane-1,6-diamine dihydrochloride The product of step (a) was treated by the method of Example 8 (b) to give the sub title compound, mp 224.8°–226.6°.

(c) 4-(2-(6-(2-(1-Naphthalenyl)ethylamino)hexylamino)ethyl)-1,2-benzenediol dihydrobromide The product of step (b) was treated by the method of Example 9 (c) to give the dihydrobromide of the title compound, mp 183.5°–185.5°.

EXAMPLE 13

4-(2-(6-(2-Cyclohexylethylamino)hexylamino)ethyl)-benzene-1,2-diol

The title compound and the following intermediates were made by the method of Example 8.

(a)
N-(2-(3,4-Dimethoxyphenyl)ethyl)-N$^1$-(2-cyclohexylethyl)hexane-1,6-diamide Colourless needles from aqueous ethanol, mp 158°–160°.

(b)
N-(2-(3,4-Dimethoxyphenyl)ethyl)-N$^1$-(2-cyclohexylethyl)hexane-1,6-diamine dihydrochloride, mp 255°–7° (dec).

(c)
4-(2-6-(2-Cyclohexylethylamine)hexylamino)ethyl)-benzene-1,2-diol dihydrobromide, mp 182.5°–183.5°.

What we claim is:

1. A method of treatment of congestive heart failure, which comprises administration to a patient suffering from such a condition of an effective amount of a compound of formula I,

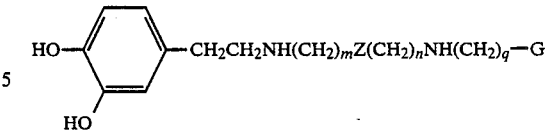

in which Z represents O, S, SO$_2$, CO, NR or a single bond, G represents a one or two ring, saturated or unsaturated carbocyclic or heterocyclic group, G being optionally substituted by phenyl, trihalomethyl or at least two groups selected from alkoxy C$_1$ to C$_6$ or halogen, provided that when Z represents a single bond, G does not represent phenyl, R represents hydrogen or alkyl C$_1$ to C$_6$,
m and n each independently represent 2, 3 or 4, and q represents an integer from 1 to 3 inclusive,
or a pharmaceutically acceptable derivative thereof.

2. A method according to claim 1, wherein G represents naphthyl, a 6-membered saturated or unsaturated carbocylic group or a ring

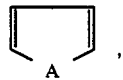

where A represents NH, O or S, G being optionally substituted by phenyl, tri-halomethyl or at least two groups selected from alkoxy C$_1$ to C$_6$ or halogen.

3. A method according to claim 1, wherein G represents naphthyl, thienyl, cyclohexenyl, cyclohexyl, phenyl; or phenyl substituted by phenyl, trihalomethyl or at least two groups selected from alkoxy C$_1$ to C$_6$ or halogen.

4. A method according to claim 1, wherein Z represents O, S or SO$_2$.

5. A method according to claim 1, wherein m and n together represent an integer from 4 to 8 inclusive.

6. A method according to claim 1, wherein q is 2.

7. A method according to claim 1, wherein said compound of formula I is selected from the group consisting of 4-(2-(2-(3-(2-Phenylethylamino)propylthio)ethylamino)ethyl)-1,2-benzenediol,
4-(2-(3-(2-(2-Phenylethylamino)ethylthio)propylamino) ethyl)-1,2-benzenediol,
4-(2-(2-(3-(2-Phenylethylamino)propoxy)ethylamino)ethyl)-1,2-benzenediol,
4-(2-(3-(2-(2-Phenylethylamino)ethoxy)propylamino)ethyl)-1,2-benzenediol,
4-(2-(2-(3-(2-Phenylethylamino)propanesulphonyl)ethylamino)ethyl-1,2benzenediol,
4-(2-(3-(2-(2-Phenylethylamino)ethanesulphonyl)ethylamino)ethyl)-1,2benzenediol,
4-(2-(6-(2-(3,4-Dimethoxyphenyl)ethylamino)hexyl amino)ethyl)-1,2-benzenoyl,
4-(2-(6-(2-(2-Thienyl)ethylamino)hexylamino)-ethyl)-1,2-benzenediol,
4-(2-(6-(2-((1,1'-Biphenyl)-4-yl)ethylamino)hexylamino)ethyl-1,2-benzenediol,
4-(2-(6-(2-(3,4-Dichlorophenyl)ethylamino)hexylamino)ethyl)-1,2-benzenediol,
4-(2-(6-(2-(3-(Trifluoromethyl)phenyl)ethylamino)hexylamino)ethyl)-1,2-benzenediol,
4-(2-(6-(2-(1-Naphthalenyl)ethylamino)hexylamino)ethyl)-1,2-benzenediol,
4-(2-(6-(2-Cyclohexylethylamino)hexylamino)ethylbenzene-1,2-diol,
and pharmaceutically acceptable acid addition salts thereof.

* * * * *